US008757145B2

(12) United States Patent
Tanaka

(10) Patent No.: US 8,757,145 B2
(45) Date of Patent: Jun. 24, 2014

(54) EJECTION HEAD CARTRIDGE AND INHALATION APPARATUS THE SAME IS ATTACHABLE THERETO

(75) Inventor: Takatoshi Tanaka, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 384 days.

(21) Appl. No.: 12/865,216

(22) PCT Filed: Apr. 15, 2009

(86) PCT No.: PCT/JP2009/057941
§ 371 (c)(1), (2), (4) Date: Jul. 29, 2010

(87) PCT Pub. No.: WO2009/128556
PCT Pub. Date: Oct. 22, 2009

(65) Prior Publication Data
US 2010/0319692 A1 Dec. 23, 2010

(30) Foreign Application Priority Data
Apr. 16, 2008 (JP) ................................ 2008-106804

(51) Int. Cl.
*A61M 15/00* (2006.01)

(52) U.S. Cl.
USPC ................ 128/200.16; 128/200.14; 239/338; 222/457.5; 222/478; 222/565

(58) Field of Classification Search
None
See application file for complete search history.

(56) References Cited

U.S. PATENT DOCUMENTS

| | | | | |
|---|---|---|---|---|
| 5,261,601 | A * | 11/1993 | Ross et al. | 239/102.2 |
| 6,196,218 | B1 * | 3/2001 | Voges | 128/200.14 |
| 6,629,524 | B1 * | 10/2003 | Goodall et al. | 128/200.14 |
| 7,073,499 | B1 * | 7/2006 | Reinhold et al. | 128/200.18 |
| 2003/0072717 | A1 * | 4/2003 | Reinhold et al. | 424/46 |
| 2006/0130829 | A1 * | 6/2006 | Sexton et al. | 128/200.23 |
| 2008/0163869 | A1 * | 7/2008 | Nobutani et al. | 128/200.23 |
| 2010/0326439 | A1 | 12/2010 | Tanaka et al. | 128/203.15 |

FOREIGN PATENT DOCUMENTS

| | | |
|---|---|---|
| EP | 1306219 | 5/2003 |
| EP | 1442764 | 8/2004 |
| JP | H08-511966 | 12/1996 |

(Continued)

OTHER PUBLICATIONS

Office Action issued Jul. 12, 2012, by Chinese (P.R. China) Patent Office in counterpart application 200980112899.3, with translation.

(Continued)

*Primary Examiner* — Jackie T Ho
*Assistant Examiner* — Eric Bryant
(74) *Attorney, Agent, or Firm* — Fitzpatrick, Cella, Harper & Scinto

(57) ABSTRACT

An ejection head cartridge and an inhalation apparatus may limit turbulence in an air stream and reduce the likelihood of collisions of ejected drug in an air flow channel so that the drug can be conveyed in a uniform air stream. An ejection head cartridge that is attachable to an inhalation apparatus for ejecting drug for inhalation by a user and has a plurality of ejection ports includes, among end portions continuous to a surface provided with the ejection ports, an end portion parallel to an ejection port array having a shape that guides a part of the air stream generated in the direction orthogonal to the ejection-port providing surface along the surface.

9 Claims, 10 Drawing Sheets

(56) References Cited

FOREIGN PATENT DOCUMENTS

| | | |
|---|---|---|
| JP | 2004-510461 | 4/2004 |
| WO | 95-01137 | 1/1995 |
| WO | WO 95-01137 | 1/1995 |

OTHER PUBLICATIONS

Office Action issued Aug. 28, 2012 by JPO in counterpart Japanese Patent Application 2008-108604 (with translation).

* cited by examiner

EJECTION HEAD CARTRIDGE AND INHALATION APPARATUS THE SAME IS ATTACHABLE THERETO

TECHNICAL FIELD

The present invention relates to an ejection head cartridge that is configured to allow a user to carry and use it, and is attachable to an inhalation apparatus for drug inhalation by the user. The present invention also relates to an inhalation apparatus to which the ejection head cartridge can be attached.

BACKGROUND ART

An inhalation apparatus has been developed, in which the principle of the ink jet method is used to eject fine liquid droplets of drug into an air flow channel, where air inhaled through a mouthpiece flows, to allow a user to inhale the drug (see Japanese Patent Application Laid-Open No. H08-511966). Such an inhalation apparatus provides an advantage that a predetermined amount of drug is precisely sprayed in the form of particles having a uniform diameter.

The general cross-section of the inhaler clearly specified in Japanese Patent Application Laid-Open No. H08-511966 is shown in FIG. 10. The inhaler includes an air inlet port 1 that introduces air to be taken from the outside into the body of a user with drug upon inhalation, an ejection head 3 that ejects the drug, and a mouthpiece 4 that the user holds in his/her mouth when inhaling the drug ejected from the ejection head 3 into the body. The ejection head 3 has ejection ports 5, and the drug, in a reservoir 7, is supplied to the ejection head 3. The inhaler is configured so that the drug is ejected in a direction generally parallel to the direction of an air stream, and the drug is conveyed without turbulence in the air stream toward an inhalation port.

The liquid droplets ejected from the ejection ports have an extremely small diameter suitable for deposition to respiratory organs, on the order of 3 μm to 8 μm, and are likely to be affected by the turbulence of an air stream in an air flow channel. The turbulence of the air stream in which the drug is conveyed may increase collisions between the liquid droplets, and increase the diameter of each liquid droplet of the inhaled drug as a result. Any change of the diameter of liquid droplets affects the site where the liquid droplets are deposited after inhalation. In addition, the turbulence may increase the tendency of the drug to become attached to the inner wall of the air flow channel. In the latter case, the amount of drug that is not inhaled after ejection is increased, resulting in waste. Such increase is not preferable from a hygienic standpoint.

The present inventors have studied an air stream in the case where the direction of drug ejection is generally parallel to the direction of the air stream, as in the case of the mentioned National Publication of International Patent Application No. 8-511966. For example, it is assumed that a cubic ejection head cartridge is installed in a cylindrical air flow channel. FIGS. 11A, 11B and 11C illustrate the simulation results on the flow of an air stream in such an air flow channel. FIG. 11C is a view illustrating flow patterns formed by liquid droplets ejected from ejection ports 5 on the same cross-section as in FIG. 11A. FIGS. 12A, 12B and 12C are views schematically illustrating the results, and FIG. 12C is a view of the air flow channel 4 and the ejection head cartridge 3 placed in the air flow channel 4 as seen from the direction of the inhalation port. An array of ejection ports 5 is arranged parallel to the direction of a longer diameter of the ellipse of a cross section of the air flow channel 4. The cross-section taken along the line 12A-12A of FIG. 12C corresponds to that taken along the line 11A-11A of FIG. 11B, and the cross-section taken along the line 12B-12B of FIG. 12C corresponds to that taken along the line 11B-11B of FIG. 11A.

The conditions used in the simulation were as follows. The aspiration rate through the inhalation port 6 was 30 L/min, so that it was assumed that air having momentum equal to the water droplets of 1.4 ml/minute was ejected through the ejection ports 5 (at a discharge rate of 1.2 L/min). The air flow channel 4 had a longer diameter of 25 mm, a shorter diameter of 10 mm, and an overall length of 25 mm, and a length from an ejection-port providing surface to the inhalation port of 15 mm. The ejection head 3 was adapted with a cube of 10 mm×10 mm×10 mm. The ejection-port providing surface included four inlet boundaries of 0.2 mm×6 mm, the longitudinal directions of which were the same as those of the ejection port arrays. The arrows in FIGS. 11A and 11B represent the vectors of wind speeds of the air flow at the start point of the arrow. That is, the length of an arrow represents the magnitude of the wind speed, and the direction of the arrow represents the direction of the air stream.

As the outlines of the results of FIGS. 11A and 11B are shown in FIGS. 12A and 12B, it was found that after the air stream that rises along the side surfaces of the ejection head cartridge 3 passes the outer peripheries of the ejection-port providing surface constituting the top head portion of the ejection head cartridge, the flow of the air stream is divided, and is likely to approach the ejection ports 5. Therefore, the air stream was found to be directed inward, and another air stream that was not parallel to the direction of drug ejection was generated. The flow patterns formed by the liquid droplets in the case where drug is conveyed in the above-described air stream are illustrated in FIG. 11C. It was found that the flow patterns formed by the liquid droplets are distributed in a narrow space at a high density because the air stream tends to be directed to the center, particularly around the outlet of the inhalation port 6.

If the air stream illustrated in the cross-sections in the direction parallel to the ejection port 5 arrays (FIG. 11A and FIG. 12A) is directed inward, the probability of collisions between the liquid droplets ejected from the ejection port arrays is increased, which is not preferable.

SUMMARY

One object of the present invention is to provide an ejection head cartridge and an inhalation apparatus that limit turbulence in an air stream and reduce the probability of collisions of ejected drug in an air flow channel so that the drug can be conveyed in a uniform air stream.

The present invention is directed to an ejection head cartridge for ejecting drug for inhalation by a user that is attachable to an inhalation apparatus and has a plurality of ejection ports. In some embodiments, among end portions continuous to a surface provided with the ejection ports (sometimes referred to herein as an “ejection-port surface” or a “port surface”), an end portion parallel to an array of the ejection ports has a shape that guides a part of the air stream generated in the direction orthogonal to the surface, along the surface.

The end portion parallel to the ejection port array can have a curved surface.

The end portion parallel to the ejection port array can have a cross-section orthogonal to the ejection port arrays that defines an obtuse angle.

As seen from above of the surface, the ejection head cartridge can have a length in which the shape turns inward toward the surface, that length being from 10% to 85% of the length of the ejection head cartridge in the direction orthogonal to the ejection port array.

The obtuse angle can be from 100° to 150°.

The ejection head cartridge can further comprise an electro-thermal conversion element that provides thermal energy, or an electro-mechanical conversion element that provides mechanical energy for ejecting the drug.

The present invention is directed to an inhalation apparatus for ejecting drug for inhalation via an inhalation port by a user, which in some embodiments may have an air flow channel that guides the ejected drug to the inhalation port, and an ejection head cartridge that has a plurality of ejection ports for ejecting the drug and is installed in the air flow channel. In some embodiments, among end portions continuous to a surface provided with the ejection ports of the ejection head cartridge, an end portion parallel to an array of the ejection ports has a shape that guides a part of the air stream generated by an inhalation by a user in the direction orthogonal to the surface along the surface. According to an ejection head cartridge and an inhalation apparatus of the present invention, among the end portions continuous to the ejection-port providing surface, an end portion parallel to an ejection port array has a shape that causes an air stream around the outer periphery of the ejection-port surface to be guided to one ejection-port surface. Thus, the likelihood of simultaneous or serial collisions between the liquid droplets ejected from the adjacent ejection ports in an air flow channel is reduced, which allows the drugs to be conveyed in a uniform air stream.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 6C is a view illustrating flow patterns formed by liquid droplets ejected from ejection ports 5 on the same cross-section as in FIG. 6A.

Figure 1A:
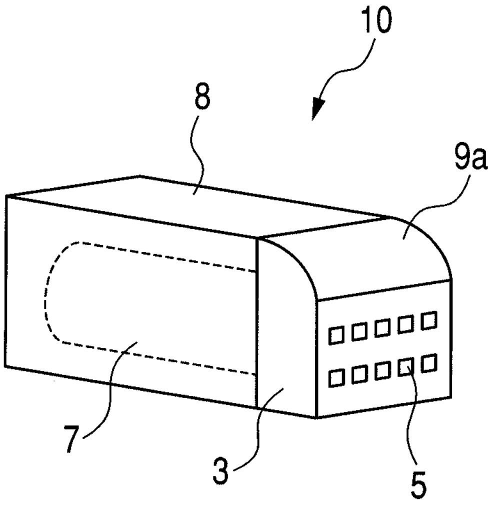
FIG. 1A is a perspective view illustrating an embodiment of an ejection head cartridge of the present invention.

In the figures, the reference numerals denote the following elements:

1 air inlet port
3 ejection head
4 air flow channel
5 ejection port
6 inhalation port (mouthpiece)
7 reservoir
8 housing
9*a*, 9*b* curved surface
9*c*, 9*d* inclined plane
10 ejection head cartridge
100 inhalation apparatus

BEST MODES FOR CARRYING OUT THE INVENTION

Preferred embodiments of the present invention will now be described in detail in accordance with the accompanying drawings. The same elements are designated by the same reference numerals.

An ejection head cartridge according to the present invention is generally adapted to have an ejection head having a plurality of ejection ports for ejecting a drug, and is a member in the form of a cartridge attachable to and detachable from an inhalation apparatus. The ejection head cartridge may be adapted to have only the ejection head portion, but may be integrated with a reservoir that holds the drug therein for ejection by an inhalation apparatus.

The top head portion includes a surface that is closest to the inhalation port when the ejection head cartridge is installed in an inhalation apparatus and constitutes an ejection-port surface provided with an array of ejection ports. In the present invention, the shapes of the end portions continuous to the ejection-port surface are appropriately designed to control a uniform air stream that flows along the side surfaces of a drug ejection cartridge, which will be described in detail below.

Preferably, the ejection head portion of the ejection head cartridge has ejection energy generating elements that is provided in either a one-to-one, one-to-many, or many-to-one relationship to the ejection ports. The elements may be electro-thermal conversion elements that provide thermal energy, or electro-mechanical conversion elements that provide mechanical energy to the drug, for example. That is, the method for ejecting the drug may be a method for providing thermal energy to drug using electro-thermal conversion elements for ejection (thermal jet method), or a method for ejecting the drug using a vibratory pressure of electro-mechanical conversion elements (e.g., piezoelectric elements) that provide mechanical energy to drug (piezojet system), for example. These methods may be sometimes referred to collectively as an "ink jet method". The ejection method may be selected depending on the drug type.

When a thermal jet method is used, with respect to each ejection head, the aperture diameter of an ejection port, the quantity of heat pulses used in ejection, the size accuracy and reproducibility of a micro-heater as an electro-thermal conversion element can be improved. This leads to a distribution of smaller diameters of liquid droplets. Also, the thermal jet method has high applicability to a compact apparatus that includes a head manufactured at a low cost and in which the head needs frequent replacement. Therefore, when portability and convenience are required in the drug ejection apparatus, particularly, the principle of ejection of the thermal jet method is preferred.

The ejection head may be those such as metered dose inhalers (MDI) and nebulizers that use the known principle for ejection.

The term "drug" as used herein includes not only any medical compound that exhibits pharmacological and physiological effects, but also ingredients, dyes, and pigments for taste and smell. The drug may be in the form of liquid or powder.

The "drug solution" as that term is used herein may be a liquid drug or a liquid medium containing the drug. The drug solution may contain any additives. The drug in the "drug solution" may be dissolved, or may be dispersed, emulsified, suspended, or in the form of a slurry, and more preferably may be homogenized in the solution.

When the drug is a drug solution, the main medium of the solution is preferably water or an organic substance, and considering the intended administration of this substance to a living body, the main medium is preferably water.

Embodiment 1

Figure 1B:
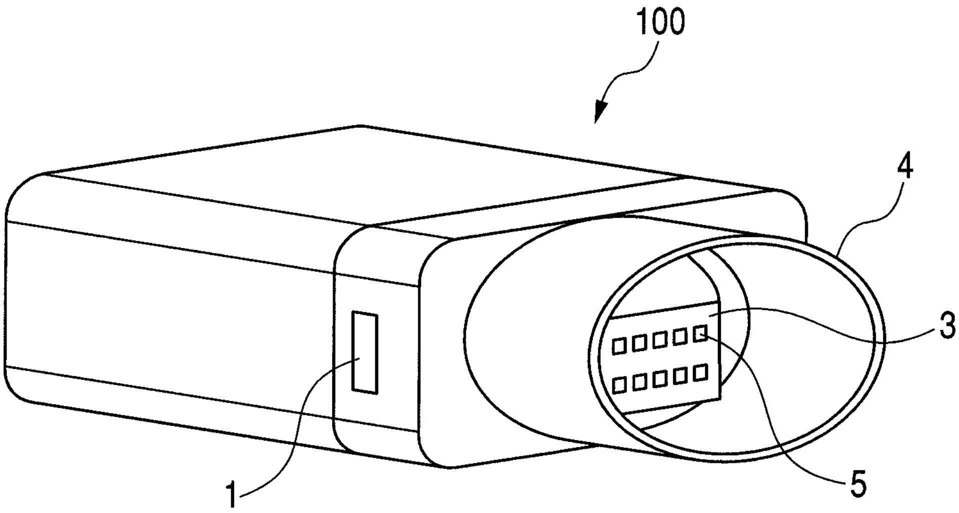
FIG. 1B is a perspective view illustrating an embodiment of an inhalation apparatus of the present invention having the ejection head cartridge attached thereto.

FIG. 1A is a perspective view illustrating an embodiment of an ejection head cartridge of the present invention. FIG. 1B is a perspective view illustrating an embodiment of an inhalation apparatus of the present invention having the ejection head cartridge attached thereto. An ejection head cartridge 10 is adapted to have an ejection head 3 and a reservoir 7 integrated with the ejection head 3. The reservoir 7 is protected by a cartridge housing 8, and the housing 8 and the ejection head 3 form the outer shape of a generally cubic form of the ejection head cartridge 10. The ejection head cartridge 10 is installed in an inhalation apparatus 100, and disposed in an air flow channel 4. The air flow channel 4 has a distal end that provides a mouthpiece that is an inhalation port held by a user in inhalation. That is, in the present embodiment, the air flow channel is integrated with a mouthpiece, which is removable from the inhalation apparatus. This enables regular cleaning and replacement.

The ejection head cartridge 10 installed to the inhalation apparatus 100 includes a top head portion that is the nearest surface of the ejection head cartridge 10 to the inhalation port and constitutes a part of the ejection head 3, and the top head portion provides an ejection-port surface in which a plurality of ejection ports 5 are formed. The ejection ports 5 are arranged in arrays (hereinafter, also referred to as "ejection port arrays" or "nozzle arrays"). In FIGS. 1A and 1B, two arrays of five ejection ports are illustrated, but these arrangements are only for a schematic illustration, and the ejection head 3 actually has 24 arrays of 558 ejection ports that have a nozzle diameter of 3 μm, for example. Below the ejection ports, a plurality of heaters (not shown) for providing thermal energy to the drug supplied from reservoir 7 to the ejection head 3 are mounted, and the heaters use the ejection mechanism based on the principle of the thermal ink jet method.

When a user takes a breath through the inhalation port, air is taken through the air inlet port 1 into the inhalation apparatus, and supplied to the air flow channel 4. The "air flow channel" is the space where the drug ejected from the ejection head 3 passes through to the inhalation port. The air supplied from air inlet port 1 to the air flow channel 4 passes along side surfaces of the ejection head cartridge 10, and is inhaled with the conveyed drug by the user.

The ejection head cartridge 10 is replaced when the remaining amount of drug in the reservoir 7 is not sufficient to provide one dose. For example, the inhalation apparatus may have a function incorporated in the main body thereof for counting the ejected amounts of the drug, so that the remaining amount can be calculated based on the ejected-amount count function. This enables issuing an announcement when it is time for replacement, and thereby replacement by the user can be urged, or ejection can be stopped until replacement is completed.

The present embodiment has a feature that, among the four end portions continuous to the square ejection-port surface, one end portion in the direction parallel to the ejection port arrays has a curved surface 9*a*. The effect of the curved surface on the air stream generated in the air flow channel 4 in an inhalation of a user will be described below.

Figure 2A:
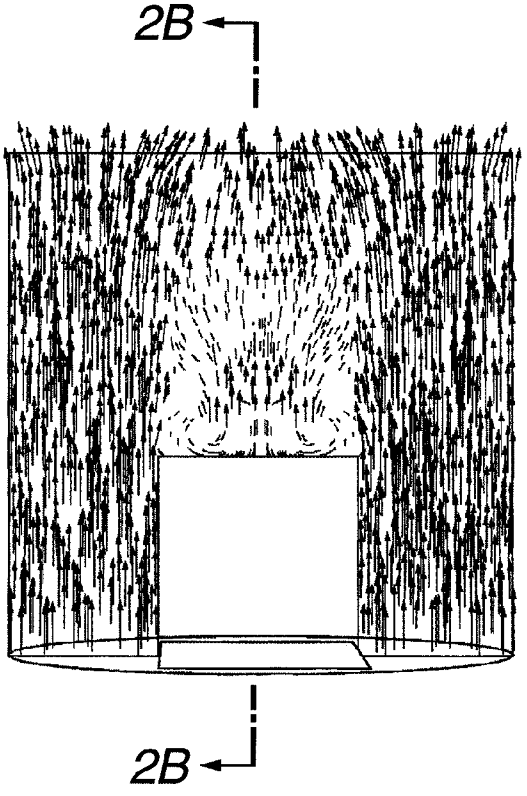
FIGS. 2A, 2B and 2C are views illustrating simulation results on an air stream in Embodiment 1 of the present invention.
Figure 2B:
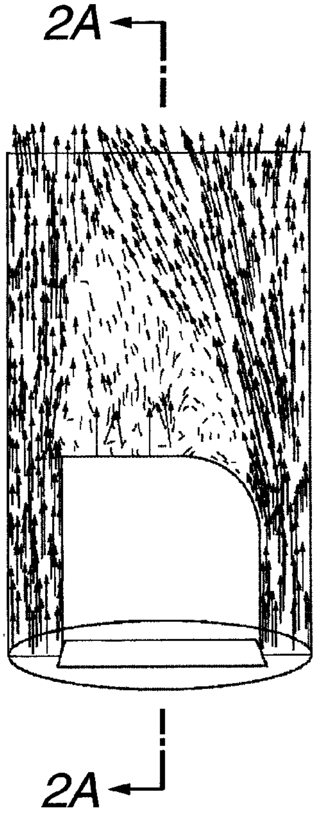
Figure 2C:
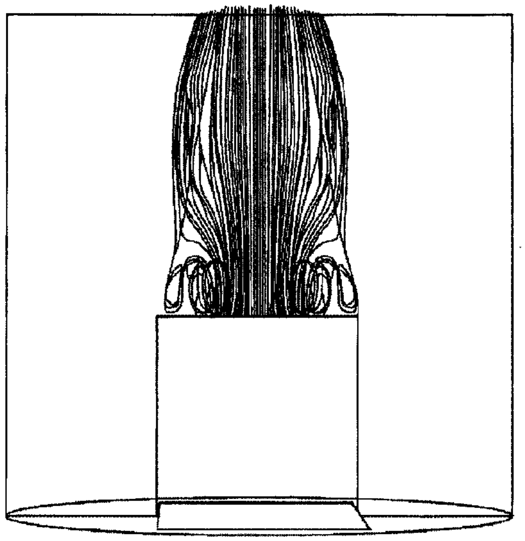
Figure 3A:
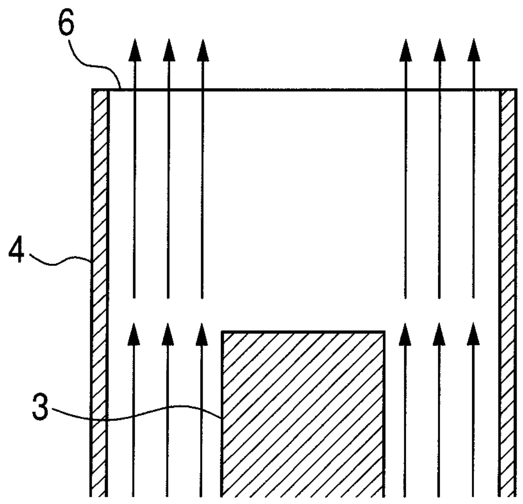
FIGS. 3A and 3B are views schematically illustrating the results of FIGS. 2A and 2B.
Figure 3B:
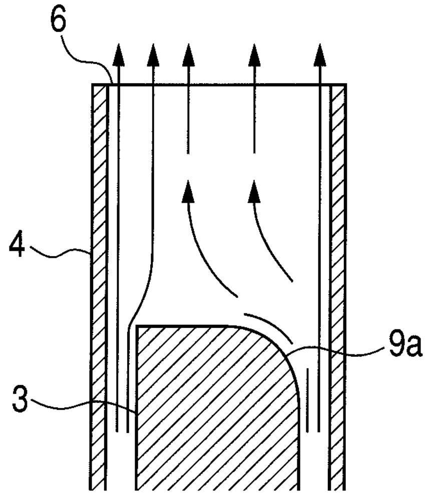
Figure 3C:
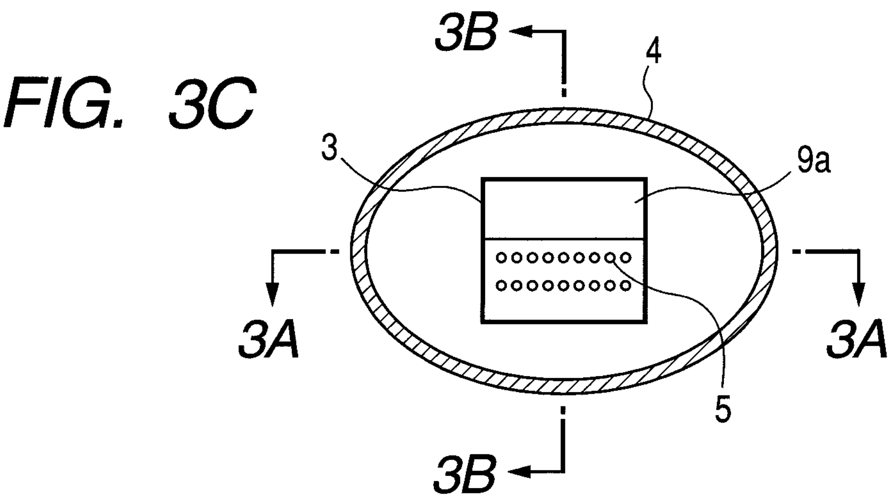
FIG. 3C is a view of an air flow channel 4 and a ejection head cartridge 3 placed in the air flow channel 4 as seen from the direction of the inhalation port.

FIGS. 2A, 2B and 2C show the simulation results on the flow of an air stream in such an air flow channel. FIG. 2C is a view illustrating flow patterns formed by liquid droplets ejected from ejection ports 5 on the same cross-section as in FIG. 2A. FIGS. 3A and 3B are views schematically illustrating the results, and FIG. 3C is a view of the air flow channel 4 and the ejection head cartridge 10 placed in the air flow channel 4 as seen from the direction of the inhalation port. The ejection port arrays are arranged parallel to the direction of the longer axis of the ellipse of a cross-section of the air flow channel 4. The cross-section taken along the line 3A-3A of FIG. 3C corresponds to that taken along the line 2A-2A of FIG. 2B. The cross-section taken along the line 3B-3B of FIG. 3C corresponds to that taken along the line 2B-2B of FIG. 2A.

The condition used in the simulation was as follows. The aspiration rate through the inhalation port 6 was 30 L/min, so that it was assumed that air having momentum equal to the water droplets of 1.4 ml/minute was ejected through the ejection ports 5 (at a discharge rate of 1.2 L/min). The air flow channel 4 had a longer diameter of 25 mm, a shorter diameter of 10 mm, and an entire length of 25 mm, and a length from the ejection-port surface to the inhalation port of 15 mm. The ejection head 3 was adapted with a cube of 10 mm×10 mm×10 mm, and a part of one of the side faces was curved. The curved surface 9*a* had a radius of curvature of 4 mm. The ejection-port surface included four inlet boundaries of 0.2 mm×6 mm, the longitudinal directions of which were the same as those of the ejection port arrays. The arrows in FIGS. 2A and 2B represent the vectors of wind speeds of the air flow at the start point of the arrow. That is, the length of an arrow represents the magnitude of the wind speed, and the direction of the arrow represents the direction of the air stream.

FIGS. 3A and 3B show the outlines of the results of FIGS. 2A and 2B. As shown in FIGS. 2B and 3B, in the back of the ejection-port surface in the inhalation apparatus, the air stream rises along the side surfaces of the ejection head cartridge 3. The air stream is generated in the direction orthogonal to the ejection-port surface. That is, the direction of drug ejection and the direction of air stream are generally parallel to each other. When it reaches around the ejection-port surface, due to the Coanda effect, the air stream is guided by the curved surface 9*a* toward the ejection-port surface, and then rises toward the inhalation port 6. Thus, the curved surface 9*a* functions as a wind guide unit that guides the air stream along the side surfaces of the cartridge 10 parallel to the ejection port arrays on the end portion side toward the center of the air flow channel 7 along the ejection-port surface.

Meanwhile, as shown in FIGS. 2A and 3A, the air stream that rises along the side surfaces orthogonal to the ejection port arrays on the end portion side is suppressed to be guided to the center of the air flow channel, in passing the ejection-port surface. First, this is because the end portion orthogonal to the ejection port arrays does not have a curved surface, and the air stream is not actively guided toward the ejection-port surface. Secondly, the air stream that rises along the side surfaces orthogonal to the ejection port arrays of the end portion cannot easily turn toward the center, because the air stream along the side surfaces parallel to the ejection port arrays of the end portion is actively guided toward the ejection-port surface and introduced into the space above that surface. Thus, the influence of a divided flow that is likely to be caused by the spread space of the air flow channel onto the air stream passing the ejection-port surface can be minimized. Therefore, the air stream that rises along the side surfaces orthogonal to the ejection port arrays on the end portion side rises without changing direction, and functions like an air curtain.

As a result, the air stream at the surface having the ejection port arrays does not bend due to the divided air stream, but the ejected drug tends to rise upward without changing direction. That is, any air stream in a direction such as would cause collisions between the liquid droplets ejected from adjacent ejection ports is unlikely to be generated, which reduces such collisions between the drug particles.

Figure 11A:
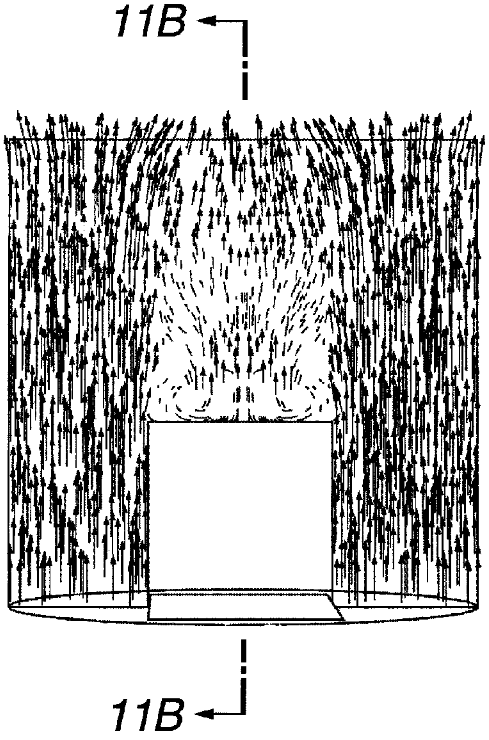
FIGS. 11A and 11B are views illustrating the simulation result on a flow of air stream when a cubic ejection head cartridge is placed in an cylindrical air flow channel.
Figure 11B:
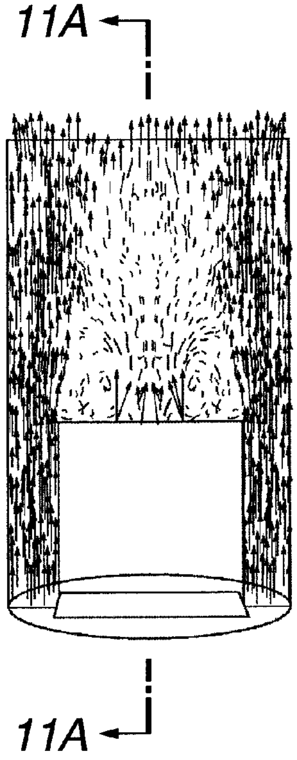
Figure 11C:
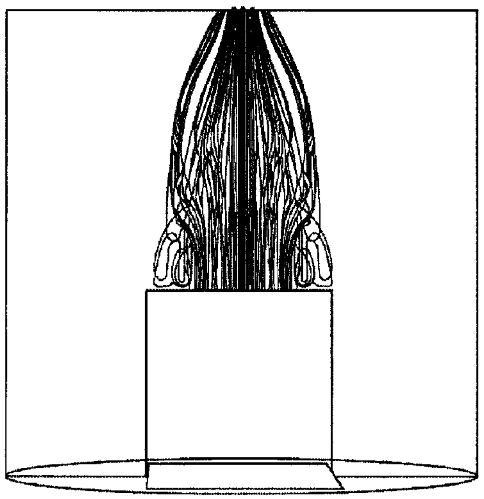
FIG. 11C is a view illustrating flow patterns formed by liquid droplets ejected from ejection ports 5 on the same cross-section as in FIG. 11A.
Figure 12A:
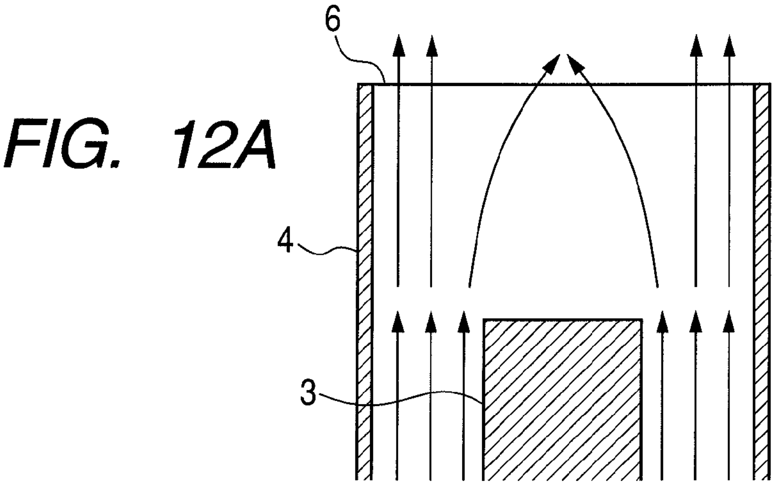
FIGS. 12A and 12B are views schematically illustrating the results of FIGS. 11A and 11B.
Figure 12B:
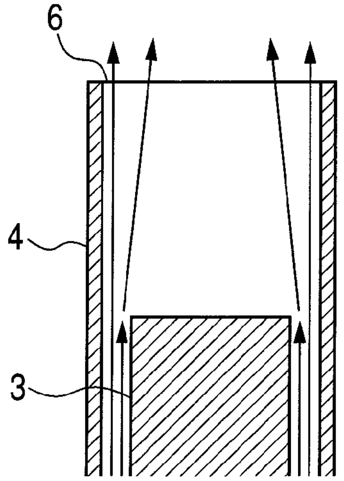
Figure 12C:
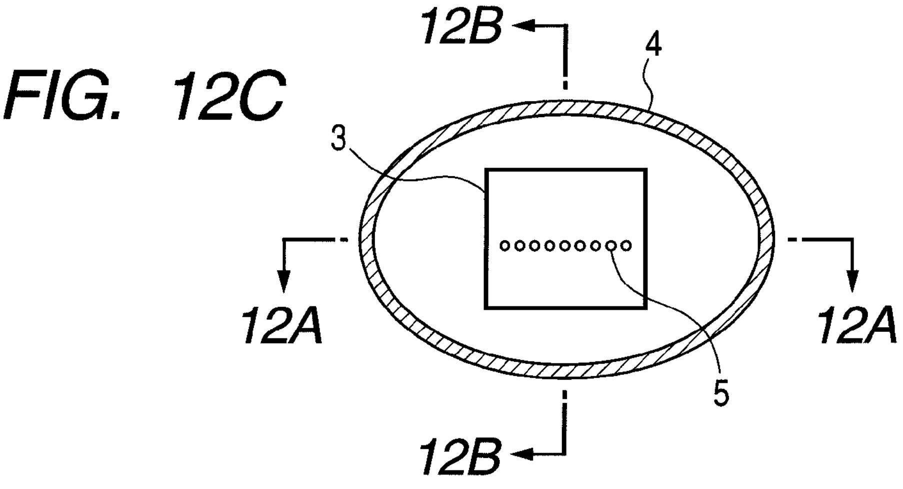
FIG. 12C is a view of the air flow channel 4 and the ejection head cartridge 3 placed in the air flow channel 4 as seen from the direction of the inhalation port.

The flow patterns formed by the liquid droplets when the drug is conveyed in the air stream are shown in FIG. 2C, but around the inhalation port 6, as compared with FIGS. 11A, 11B and 11C, the flow patterns illustrating the paths of the liquid droplets are distributed within a broader range in the mouthpiece 4. This also demonstrates that the probability of collisions between liquid droplets is reduced.

Generally, the ejection ports of one ejection port array are separated by intervals of several μm to tens of μm, but the arrays are separated by intervals of several μm to several mm. In the case where a plurality of ejection port arrays are provided, the number of ejection ports in the direction parallel to the ejection port arrays is larger than the number of ejection ports in the direction orthogonal to the ejection port arrays. Thus, the above configuration enables the reduction of the likelihood of collisions between liquid droplets ejected from different ejection ports, resulting in the supply of particles of drug having a uniform diameter into the user's body.

The array of ejection ports in the present invention is not always in a straight line. The array may include a zigzag part or a circular part as long as the nozzles are specifically arranged in a line in one direction. Comparing the intervals between the ejection ports with the intervals between the arrays that are seen recently, because the latter is larger, a series of ejection ports that slightly deviate from a straight line can be considered as an ejection port array. In such an ejection port array, no ejection ports are positioned along the same vertical direction. The same is applied to Embodiment 2.

Figure 4:
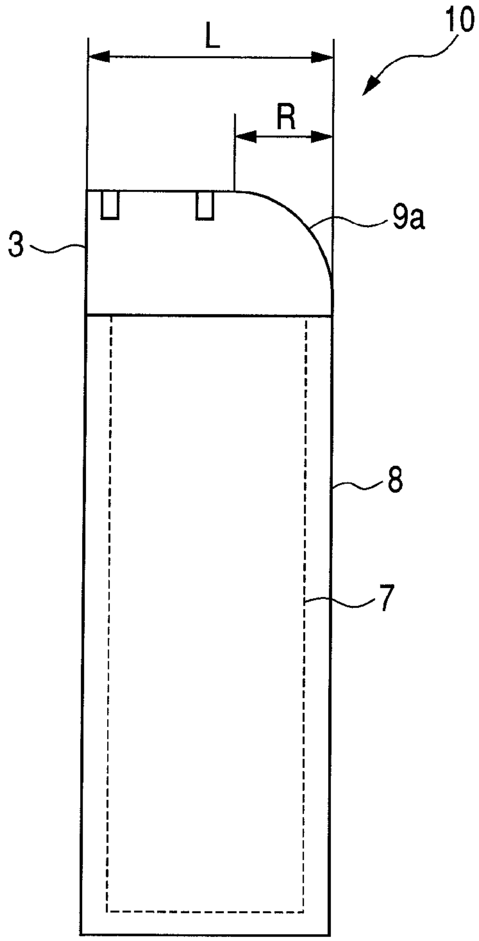
FIG. 4 is a cross-sectional view of an ejection head cartridge 10 of Embodiment 1 taken along a plane orthogonal to ejection port array.

Next, an exemplary embodiment of a shape of the curved surface will be described below. FIG. 4 is a cross-sectional view of an ejection head cartridge 10 taken along a plane orthogonal to the ejection port arrays. The ejection head cartridge 10 has a length L in the direction orthogonal to the ejection port arrays. As seen from above of the ejection-port surface, the ejection head cartridge 10 has a length R in which the curved surface 9*a* turns inward toward the ejection-port providing surface. That is, the ejection-port providing surface has a length defined as L-R in the direction orthogonal to the ejection port arrays. In order to effectively guide the air stream to the center in the air flow channel 4, the length R is preferably 10% of the length L or more, and more preferably 25% or more. In addition, from the viewpoint of the appropriate number of ejection ports for an amount of ejection, the length R is preferably 85% or less, and more preferably 70% or less.

Figure 5:
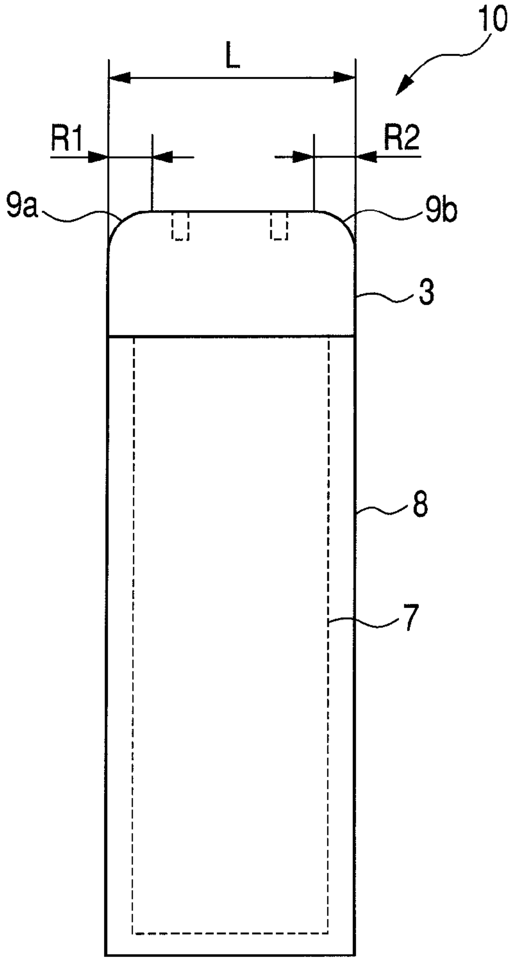
FIG. 5 is a cross-sectional view of the ejection head cartridge 10 in a case where curved surfaces are provided to two side surfaces of end portions parallel to the ejection port arrays of the Embodiment 1.

In the present embodiment, the case where only one curved surface is provided at the end portion among the end portions in the direction parallel to the ejection port arrays has been described, but the present embodiment is not limited to such a case, and may have curved surfaces 9*a* and 9*b* on the two side surfaces. FIG. 5 is a cross-sectional view of the ejection head cartridge 10 in a case where curved surfaces are provided to two side surfaces of the end portions parallel to the ejection port arrays. In the case, the length R is defined as the sum of the lengths R1 and R2 by which the curved surfaces 9*a* and 9*b* respectively turn inward toward the ejection-port providing surface. In this case also, in order to effectively guide the air stream to the center in the air flow channel 4, the length R is preferably 10% of the length L or more, and more preferably 25% or more. In addition, from the viewpoint of the appropriate number of ejection ports for an amount of ejection, the length R is preferably 85% or less, and more preferably 70% or less.

Among the end portions parallel to the ejection port arrays, the portion having the curved surface is preferably provided for a length equal to the length of the ejection port arrays or more.

Embodiment 2

In a second embodiment of the present invention, an end portion parallel to an ejection port array has a cross-section that is orthogonal to the ejection port array and defines an obtuse angle. That is, as shown in FIG. 9 to FIGS. 12A, 12B and 12C, at least one of the side surfaces parallel to the ejection port array has an inclined plane 9*c*. The effect of the inclined plane 9*c* onto the air stream generated in the air flow channel 4 in inhalation of a user will be described below.

Figure 6A:
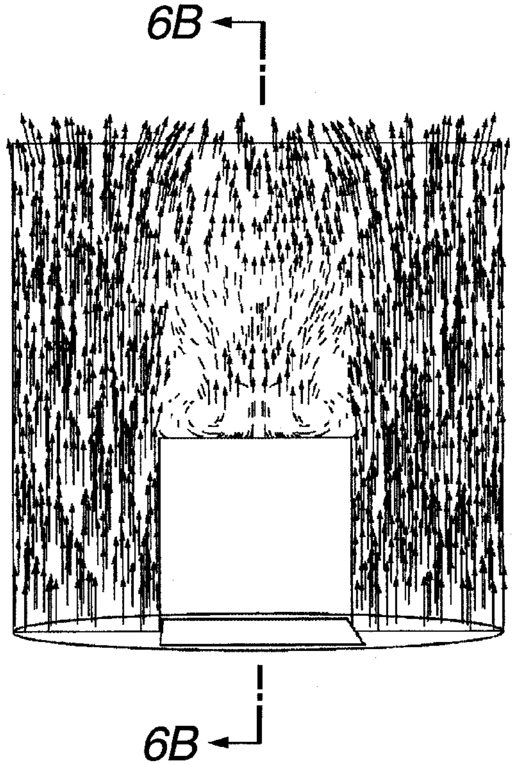
FIGS. 6A, 6B and 6C are views illustrating simulation results on the air stream in Embodiment 1 of the present invention.
Figure 6B:
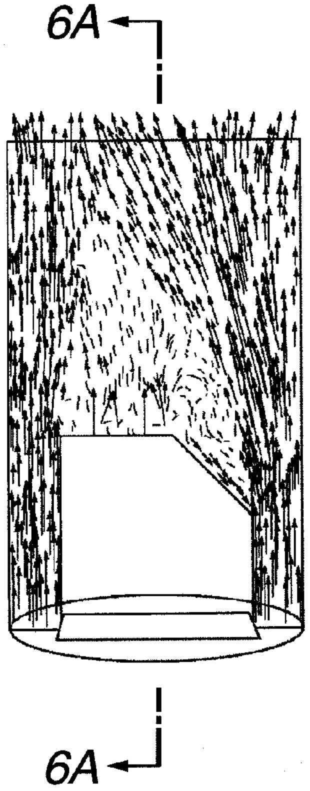
Figure 6C:
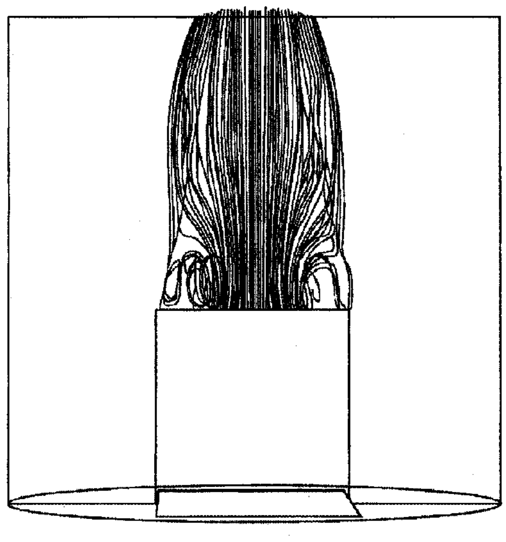
Figure 7A:
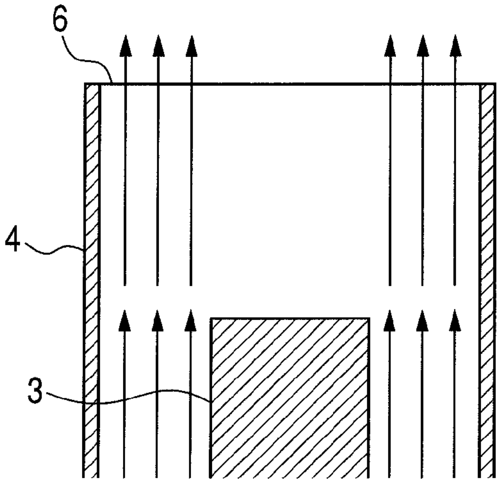
FIGS. 7A and 7B are views schematically illustrating the results of FIGS. 6A and 6B.
Figure 7B:
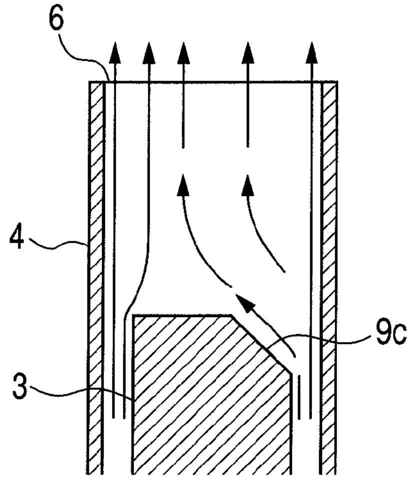
Figure 7C:
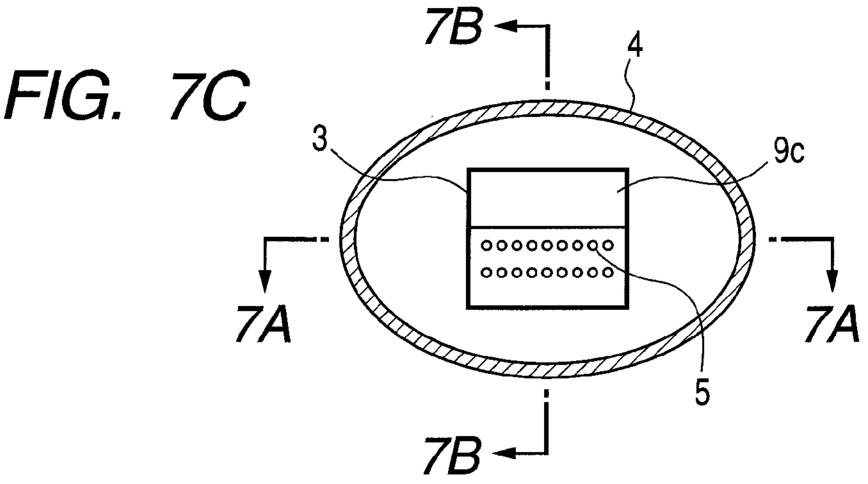
FIG. 7C is a view of the air flow channel 4 and the ejection head cartridge 3 placed in the air flow channel 4 as seen from the direction of the inhalation port.

FIGS. 6A, 6B and 6C show the simulation results on the flow of an air stream in such an air flow channel. FIG. 6C is a view illustrating flow patterns formed by liquid droplets ejected from ejection ports 5 on the same cross section as in FIG. 6A. FIGS. 7A and 7B are views schematically illustrating the results, and FIG. 7C is a view of the air flow channel 4 and the ejection head cartridge 10 placed in the air flow channel 4 as seen from the direction of the inhalation port. The ejection port arrays are arranged parallel to the direction of a longer diameter of the ellipse of a cross-section of the air flow channel 4. The cross-section taken along the line 7A-7A of FIG. 7C corresponds to that taken along the line 6A-6A of FIG. 6B. The cross-section taken along the line 7B-7B of FIG. 7C corresponds to that taken along the line 6B-6B of FIG. 6A.

The condition used in the simulation was as follows. The aspiration rate from the inhalation port 6, the discharge rate from the ejection ports 5, and the dimensions of the air flow channel 4 were similar to those in Embodiment 1. In the present embodiment, the ejection head 3 is adapted to have a cube of 10 mm×10 mm×10 mm, and a part of one of the side faces has an inclination 9*c*. The length (T in FIG. 8) by which the inclined plane turns inward toward the ejection-port providing surface was set to be 4 mm.

As seen from the above figures, in the present embodiment, the inclined plane 9*c* provides the operational effects as those of the curved surface 9*a* in Embodiment 1. As a result, the ejected drug tends to rise upward without changing direction. That is, an air stream in a direction such as would be likely to cause collisions between the liquid droplets ejected from adjacent ejection ports is unlikely to be generated, which reduces collisions between the drug particles.

The flow patterns formed by the liquid droplets when the drug is conveyed by the air stream is shown in FIG. 6C, but similarly to Example 1, as compared with FIGS. 11A, 11B and 11C, the flow patterns illustrating the paths of the liquid droplets are distributed within a broader range in the aspiration flow channel 2 around the inhalation port 6. This also demonstrates that the likelihood of collisions between liquid droplets is reduced.

That is, the inclined plane at the end portion parallel to the ejection port arrays provides an obtuse angle to a cross-section orthogonal to the ejection port arrays of the end portion parallel to the ejection port arrays. This configuration enables the flow of ejected drug in a uniform air stream.

Figure 8:
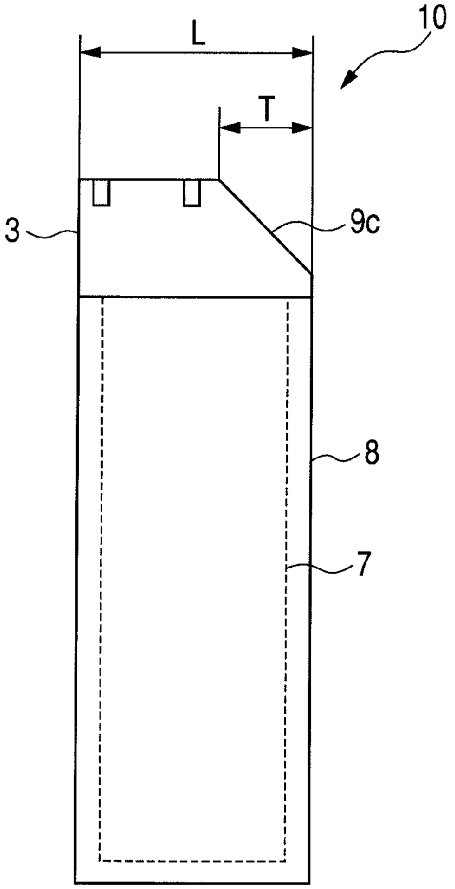
FIG. 8 is a cross-sectional view of an ejection head cartridge 10 of Embodiment 2 taken along a plane orthogonal to the ejection port array.

Next, an exemplary embodiment of the shape of the inclined plane will be described. FIG. 8 is a cross-sectional view of the ejection head cartridge 10 of the present embodiment taken along a plane orthogonal to the ejection port arrays. The ejection head cartridge 10 has a length L in the direction orthogonal to the ejection port arrays. As seen from above of the ejection-port providing surface, the ejection head cartridge 10 has a length T in which the inclined plane 9*c* turns inward toward the ejection-port providing surface. That is, the ejection-port providing surface has a length defined as L-T in the direction orthogonal to the ejection port arrays. In order to effectively guide the air stream to the center in the air flow channel 4, the length T is preferably 10% of the length L or more, and more preferably 25% or more. In addition, from the viewpoint of the appropriate number of ejection ports for an amount of ejection, the length T is preferably 85% or less, and more preferably 70% or less.

Also, the obtuse angle of the cross-section orthogonal to the ejection port arrays of the end portion parallel to the ejection port arrays is preferably from 100° to 150°, more preferably 120° to 140° from the viewpoint of the minimum turbulence in the air stream.

Figure 9:
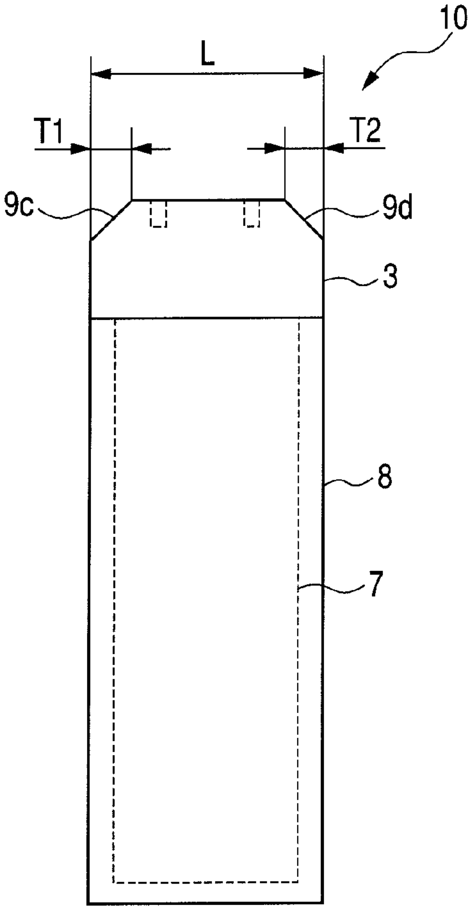
FIG. 9 is a cross-sectional view of the ejection head cartridge 10 in a case where two side surfaces of the end portions parallel to the ejection port arrays individually have an inclined plane.
Figure 10:
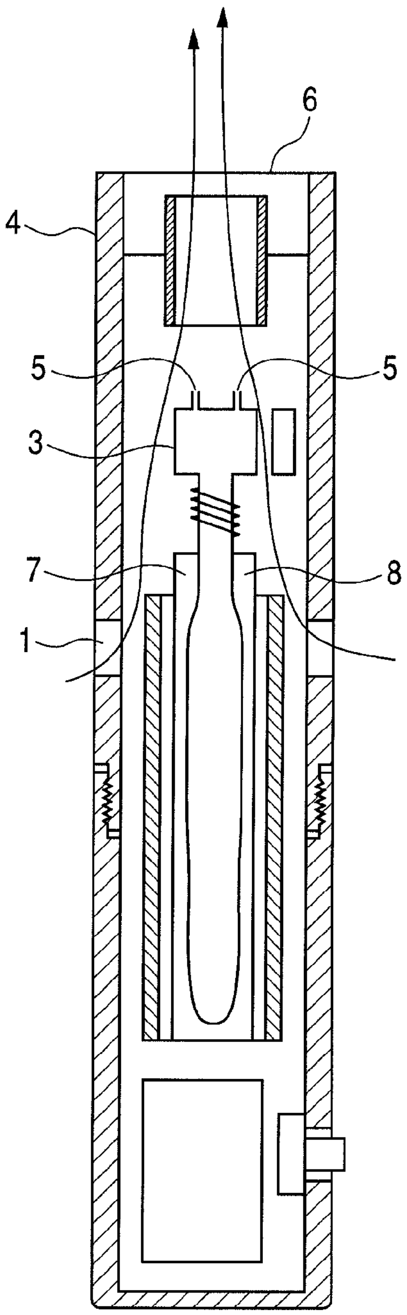
FIG. 10 is a general cross-sectional view of an inhaler as described in Patent Document 1 of the prior art.

In the present embodiment, both side surfaces of the end portions parallel to the ejection port arrays may individually have an inclined plane. FIG. 9 is a cross-sectional view of the ejection head cartridge 10 in a case where the inclined planes 9*c* and 9*d* are provided at two side surfaces of the end portions parallel to the ejection port arrays. In the case, the length T is defined as the sum of the lengths T1 and T2 by which the curved surfaces 9*a* and 9*b* respectively turn inward toward the ejection-port providing surface. In this case also, in order to effectively guide the air stream to the center in the air flow channel 4, the length T is preferably 10% of the length L or more, and more preferably 25% or more. In addition, from the viewpoint of the appropriate number of ejection ports for an amount of ejection, the length T is preferably 85% or less, and more preferably 70% or less.

An ejection head cartridge of the present invention can be used in various applications other than an inhalation apparatus for drug inhalation. For example, an ejection head cartridge of the present invention can be used in an apparatus for spraying fragrance, an inhalation apparatus for tastes such as nicotine, and the like. Thus, an ejection head cartridge of the present invention can be used in various applications that require reliable and hygienic ejection.

The present invention is not limited to the above embodiments and various changes and modifications can be made within the spirit and scope of the present invention. Therefore to apprise the public of the scope of the present invention, the following claims are made.

This application claims the benefit of Japanese Patent Application No. 2008-106804, filed Apr. 16, 2008, which is hereby incorporated by reference herein in its entirety.

The invention claimed is:

1. An ejection head cartridge adapted for ejecting a drug for inhalation by a user, comprising: an attachment portion having a shape attachable to an inhalation apparatus; and an ejection-port surface having a plurality of ejection ports disposed in an array, said ejection-port surface having an end portion running parallel to said array of said plurality of ejection ports, said end portion having a curved surface, wherein, as seen from above said ejection-port surface, the ejection head cartridge has a length in a direction orthogonal to said array of said plurality of ejection ports, and said ejection-port surface excluding said end portion has a width in the direction orthogonal to said array of said plurality of ejection ports, said width being from 15% to 90% of said length.

2. An ejection head cartridge adapted for ejecting a drug for inhalation by a user, comprising: an attachment portion having a shape attachable to an inhalation apparatus; an ejection-port surface having a plurality of ejection ports disposed in an array, said ejection-port surface having an end portion running parallel to said array of said plurality of ejection ports, wherein said end portion has a beveled surface having a cross-section orthogonal to said array of said plurality of ejection ports that defines an obtuse angle, and wherein, as seen from above said ejection-port surface, the ejection head cartridge has a length in a direction orthogonal to said array of said plurality of ejection ports, and said ejection-port surface excluding said end portion has a width in the direction orthogonal to said array of said plurality of ejection ports, said width being from 15% to 90% of said length.

3. The ejection head cartridge according to claim 2, wherein said obtuse angle is from 100° to 150°.

4. The ejection head cartridge according to claim 1, further comprising an electro-thermal conversion element that provides thermal energy or an electro-mechanical conversion element that provides mechanical energy for ejecting the drug.

5. An inhalation apparatus adapted for ejecting a drug for inhalation via an inhalation port by a user, comprising: an air flow channel that guides an ejected drug to the inhalation port; and an ejection head cartridge that is installed in said air flow channel, wherein said ejection head cartridge comprised of an attachment portion having a shape attachable to an inhalation apparatus; and an ejection-port surface having a plurality of ejection ports disposed in an array, said ejection-port surface having an end portion running parallel to said array of said plurality of ejection ports, said end portion having a curved surface, wherein, as seen from above said ejection-port surface, the ejection head cartridge has a length in a direction orthogonal to said array of said plurality of ejection ports, and said ejection-port surface excluding said end portion has a width in the direction orthogonal to said array of said plurality of ejection ports, said width being from 15% to 90% of said length.

6. An inhalation apparatus adapted for ejecting a drug for inhalation via an inhalation port by a user, comprising: an air flow channel that guides an ejected drug to the inhalation port; and an ejection head cartridge that is installed in said air flow channel, wherein said ejection head cartridge is comprised of an attachment portion having a shape attachable to an inhalation apparatus; an ejection-port surface having a plurality of ejection ports disposed in an array, said ejection-port surface having an end portion running parallel to said array of said plurality of ejection ports, wherein said end portion has a beveled surface having a cross-section orthogonal to said array of said plurality of ejection ports that defines an obtuse angle, and wherein, as seen from above said ejection-port surface, the ejection head cartridge has a length in a direction orthogonal to said array of said plurality of ejection ports, and said ejection-port surface excluding said end portion has a width in the direction orthogonal to said array of said plurality of ejection ports, said width being from 15% to 90% of said length.

7. The ejection head cartridge according to claim 2, further comprising an electro-thermal conversion element that provides thermal energy or an electro-mechanical conversion element that provides mechanical energy for ejecting the drug.

8. The ejection head cartridge according to claim 1, wherein said plurality of ejection ports are arranged in a number of a plurality of rows on said ejection-port surface and a number of ejection ports in the plurality of rows is larger than the number of said plurality of rows.

9. The ejection head cartridge according to claim 2, wherein said plurality of ejection ports are arranged in a number of a plurality of rows on said ejection-port surface and a number of ejection ports in the plurality of rows is larger than the number of said plurality of rows.

* * * * *